(12) United States Patent
Ozawa et al.

(10) Patent No.: US 8,564,651 B2
(45) Date of Patent: Oct. 22, 2013

(54) ENDOSCOPE APPARATUS AND ILLUMINATION CONTROL METHOD OF ENDOSCOPE APPARATUS

(75) Inventors: Satoshi Ozawa, Kanagawa (JP); Takayuki Iida, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 450 days.

(21) Appl. No.: 12/888,819

(22) Filed: Sep. 23, 2010

(65) Prior Publication Data

US 2011/0069163 A1 Mar. 24, 2011

(30) Foreign Application Priority Data

Sep. 24, 2009 (JP) ................. P2009-219246

(51) Int. Cl.
*A61B 1/04* (2006.01)
(52) U.S. Cl.
USPC .......................................................... 348/68
(58) Field of Classification Search
USPC .......................................................... 348/68
See application file for complete search history.

(56) References Cited

U.S. PATENT DOCUMENTS

| 2003/0036785 | A1* | 2/2003 | Ii et al. ........................ 607/89 |
| 2006/0235277 | A1 | 10/2006 | Ohkubo et al. |
| 2009/0062617 | A1 | 3/2009 | Mizuyoshi |
| 2009/0306478 | A1* | 12/2009 | Mizuyoshi .................... 600/178 |
| 2010/0268091 | A1* | 10/2010 | Takaoka ........................ 600/478 |

FOREIGN PATENT DOCUMENTS

| EP | 1 898 677 A2 | 3/2008 |
| JP | 2006-136453 A | 6/2006 |
| JP | 2006-296656 A | 11/2006 |
| JP | 2007-264537 A | 10/2007 |
| JP | 2009-56248 | 3/2009 |
| JP | 2009-131324 A | 6/2009 |
| JP | 2009-189473 A | 8/2009 |
| WO | WO 2004/080291 A2 | 9/2004 |

OTHER PUBLICATIONS

European Search Report dated Jan. 28, 2011.
Japanese Office Action dated Feb. 26, 2013, with English translation.

* cited by examiner

*Primary Examiner* — Richard Torrente
(74) *Attorney, Agent, or Firm* — McGinn IP Law Group, PLLC

(57) ABSTRACT

Provided are a plurality of semiconductor light emitting elements having different central light emission wavelengths, a multiplexer means for multiplexing lights, and a central wavelength converting means for controlling a light emission amount ratio of the plurality of semiconductor light emitting elements by the use of a wavelength conversion table in which a central wavelength of multiplexed laser light is obtained on the basis of information of a light emission amount and the central light emission wavelengths. Accordingly, the central wavelength of the multiplexed light is controlled to be a predetermined wavelength.

4 Claims, 11 Drawing Sheets

ENDOSCOPE APPARATUS AND ILLUMINATION CONTROL METHOD OF ENDOSCOPE APPARATUS

The present application claims priority from Japanese Patent Application No. 2009-219246 filed on Sep. 24, 2009, the entire content of which is incorporated herein by reference.

BACKGROUND OF INVENTION

1. Field of the Invention

The present invention relates to an endoscope apparatus and an illumination control method of the endoscope apparatus.

2. Description of the Related Art

For example, JP-A-2006-296656 discloses an endoscope apparatus including an illumination means for emitting laser light from a semiconductor light emitting element to a fluorescent substance so as to perform white illumination by exciting the fluorescent substance to emit light. According to this kind of endoscope apparatus, by using the laser light, it is possible to obtain high illumination light which has lower power consumption than that of a halogen lamp or xenon lamp. However, in the semiconductor light emitting element, even in a product having the same specification, there is differences in the light emission wavelength in accordance with the conditions of the manufacturing process or the materials to be used. Due to differences in the light emission wavelength, the light emission efficiency of the fluorescent substance may be reduced even by a slight difference in the wavelength in accordance with the material of the fluorescent substance. In this case, since the energy applied to the semiconductor light emitting element needs to be increased in order to obtain a predetermined light amount, needless energy loss occurs.

Particularly, in the case where the absorption spectrum of the fluorescent substance in a blue wavelength bandwidth is a rapid profile, the light emission efficiency of the fluorescent substance is increased or decreased due to a slight variation in the light emission wavelength of the semiconductor light emitting element. As a result, even when the fluorescent substance is illuminated by the same light emission intensity, the light emission intensity of the fluorescent substance is reduced, and hence bluish-white illumination is performed. Likewise, due to differences in the light emission wavelength, a difference occurs in the light emission spectrum of the white light formed by the laser light and the excitation light, and variations occur in the tone of the image, thereby causing a problem in that a correct diagnosis may be impeded.

In addition, the spectral sensitivity of the imaging element may be easily and largely deteriorated around 400 nm. In the case of using the semiconductor light emitting element having a short wavelength substantially equal to 400 nm, a slight difference in the light emission wavelength influences the light receiving sensitivity of the imaging element. For this reason, the wavelength of the light emitted from the semiconductor light emitting element needs to be maintained with high precision to be a stipulated constant value.

Further, in the manufacturing process of the semiconductor light emitting element, a product inspection step is performed after manufacturing so as to remove through inspection products which are out of the stipulated light emission wavelength range, and only products having similar quality levels are supplied to the market. Accordingly, the cost of the components of the semiconductor light emitting element tends to easily increase, which impedes a decrease in the cost of the endoscope apparatus.

SUMMARY OF INVENTION

An object of the present invention is to prevent deterioration in the illumination light amount or imaging sensitivity and to reduce the cost of components of an endoscope apparatus. The endoscope apparatus and its illumination control method are capable of highly precisely maintaining a wavelength of light emitted from a semiconductor light emitting element at a stipulated constant value and generating laser light of a stipulated wavelength even with a single semiconductor light emitting element the light emission wavelength of which is not included in a stipulated wavelength range.

The present invention has the following configuration.

(1) An endoscope apparatus including: an endoscope which includes an illumination optical system having a fluorescent substance; a light source unit which is connected to the endoscope, includes a plurality of semiconductor light emitting elements having different central light emission wavelengths, and supplies light from the semiconductor light emitting elements to the illumination optical system; a multiplexer means for multiplexing the lights output from the plurality of semiconductor light emitting elements; and a central wavelength converting means for controlling the light emission amount ratio of the plurality of semiconductor light emitting elements and converting the central wavelength of the light multiplexed by the multiplexer means.

(2) An illumination control method of an endoscope apparatus including an endoscope which includes an illumination optical system having a fluorescent substance; and a light source unit which is connected to the endoscope, includes a plurality of semiconductor light emitting elements having different central light emission wavelengths, and supplies light from the semiconductor light emitting elements to the illumination optical system, the illumination control method including at least the steps of: measuring the central light emission wavelength of each of the semiconductor light emitting elements; obtaining a central wavelength of light formed by multiplexing the lights output from the plurality of semiconductor light emitting elements in accordance with setting values of the central light emission wavelength of each of the semiconductor light emitting elements and a light emission amount of each of the semiconductor light emitting elements, and registering the central wavelength in a wavelength conversion table; determining the light emission amount ratio of the semiconductor light emitting elements so that the central wavelength of the multiplexed light is equal to a target wavelength on the basis of the wavelength conversion table; and driving the semiconductor light emitting elements in accordance with the determined light emission amount ratio.

According to the endoscope apparatus and the illumination control method of the endoscope apparatus of the present invention, it is possible to highly precisely maintain the wavelength of the light emitted from the semiconductor light emitting element to be a stipulated constant value. In addition, even in the single semiconductor light emitting element having the light emission wavelength not included in the stipulated wavelength range, it is possible to generate the light of the stipulated wavelength in such a manner that the light emission amount ratio is controlled by the combination of the plurality of semiconductor light emitting elements. Accordingly, it is possible to prevent deterioration of the illumination light amount or imaging sensitivity, and to reduce the cost of components of the endoscope apparatus.

DESCRIPTION OF EXEMPLARY EMBODIMENTS

Hereinafter, an embodiment of the invention will be described with reference to the accompanying drawings.

Figure 1:
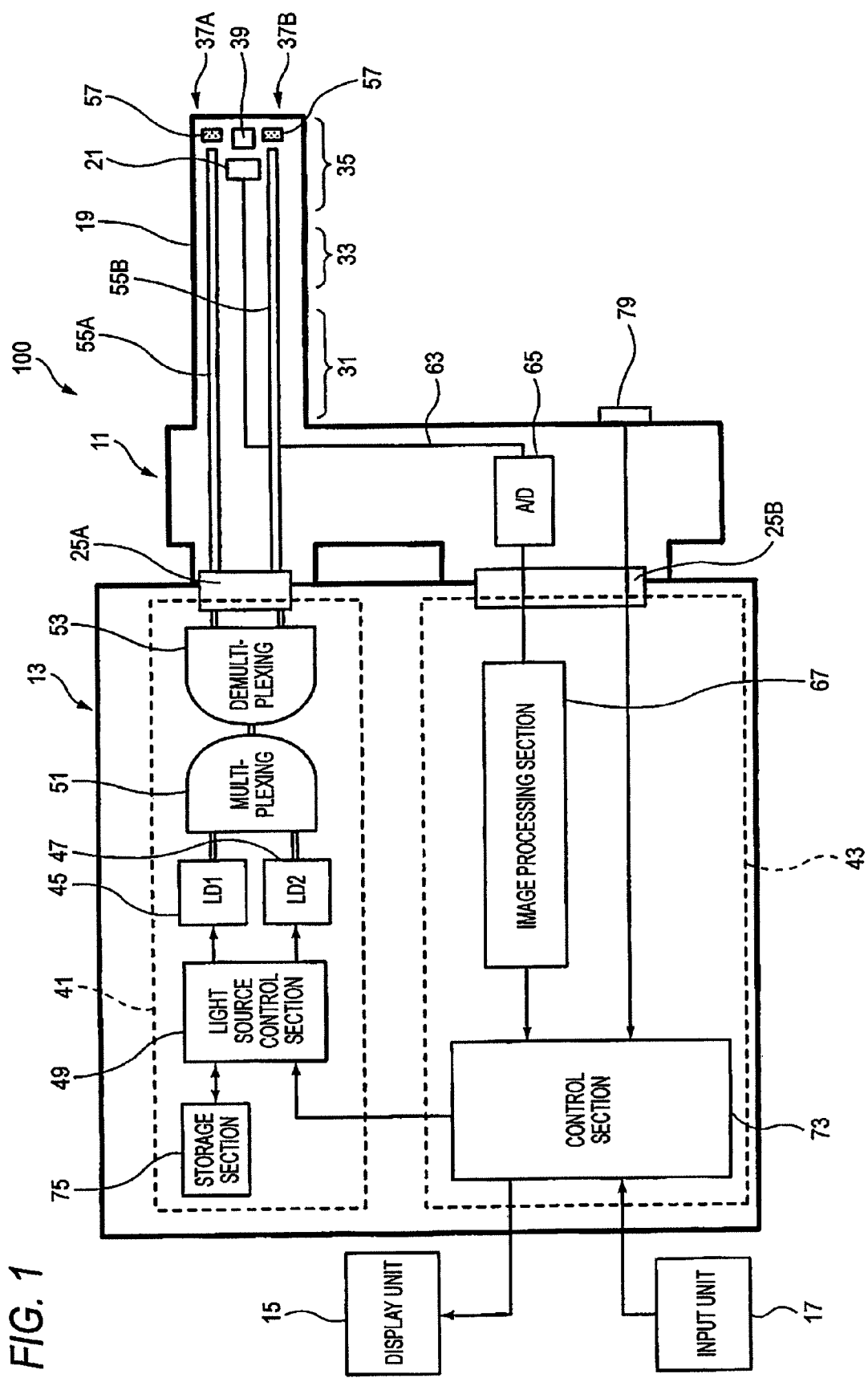
FIG. 1 is a diagram illustrating an embodiment of the present invention, and is a conceptual block diagram of an endoscope apparatus.
Figure 2:
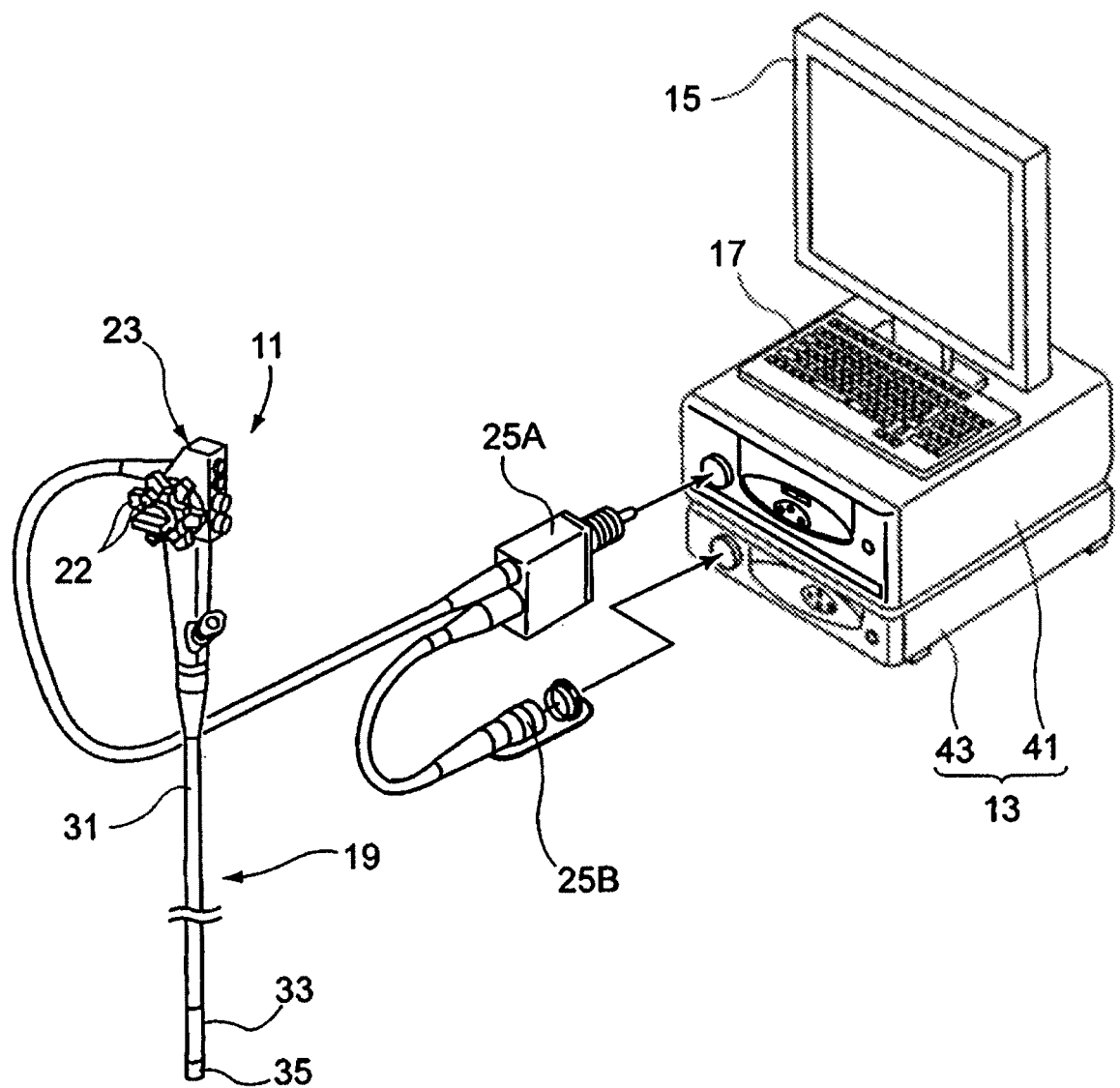
FIG. 2 is an external view as an example of the endoscope apparatus shown in FIG. 1.

FIG. 1 is a diagram illustrating an embodiment of the invention, and is a conceptual block diagram of an endoscope apparatus. FIG. 2 is an external view of an example of the endoscope apparatus shown in FIG. 1.

As shown in FIGS. 1 and 2, an endoscope apparatus 100 includes an endoscope 11, and a control device 13 to which the endoscope 11 is connected. The control device 13 is connected to a display unit 15 which displays image information or the like, and an input unit 17 which receives an input operation. The endoscope 11 is an electronic endoscope which includes an illumination optical system emitting an illumination light from a front end of an endoscope insertion unit 19 and an imaging optical system including an imaging element 21 (refer to FIG. 1) configured to image an observation area.

In addition, the endoscope 11 includes the endoscope insertion unit 19 which is inserted into a test object, an operation unit 23 (refer to FIG. 2) which is used for an operation of curving the front end of the endoscope insertion unit 19 or an observation operation, and connectors 25A and 25B which are used to attachably/detachably connect the endoscope 11 to the control device 13. In addition, although not shown in the drawings, the inside of the operation unit 23 and the endoscope insertion unit 19 is provided with various channels such as a clamp channel used for inserting a tissue pickup treatment tool or the like therethrough or an air/water feeding channel.

The endoscope insertion unit 19 includes a flexible portion 31 which has flexibility, a curved portion 33, and a front end portion (hereinafter, referred to as an endoscope front end portion) 35. As shown in FIG. 1, the endoscope front end portion 35 is provided with illumination ports 37A and 37B which are used to emit a light to the observation area, and an imaging sensor 21 such as a CCD (Charge Coupled Device) image sensor or a CMOS (Complementary Metal-Oxide Semiconductor) image sensor which is used to acquire image information of the observation area. The light receiving surface of the imaging element 21 is provided with an object lens unit 39.

The curved portion 33 is provided between the flexible portion 31 and the front end portion 35, and is adapted to be curved by a rotation operation of an angle knob 22 disposed in the operation unit 23. The curved portion 33 may be curved to an arbitrary direction and an arbitrary angle in accordance with a portion of the test object examined by the endoscope 11. The observation direction of the illumination ports 37A and 37B and the imaging element 21 of the endoscope front end portion 35 may be directed to a desired observation portion. In addition, the illumination ports 37A and 37B of the endoscope insertion unit 19 are provided with a cover glass or a lens (not shown).

The control device 13 includes a light source device 41 which generates an illumination light supplied to the illumination ports 37A and 37B of the endoscope front end portion 35, and a processor 43 which performs an image process on an image signal generated from the imaging element 21, and is connected to the endoscope 11 via the connectors 25A and 25B. In addition, the processor 43 is connected to the display unit 15 and the input unit 17 which are described above. The processor 43 performs an image process on an imaging signal transmitted from the endoscope 11 on the basis of the command from the operation unit 23 of the endoscope 11 or the input unit 17 thereof, and generates and supplies a display image to the display unit 15.

The light source device 41 includes two blue laser light sources 45 and 47 which generate a blue laser light in which the central wavelength is stipulated as about 445 nm. In these blue laser light sources 45 and 47, for example, a semiconductor light emitting element LD1 having a central wavelength of 444 nm is provided as a light emission source of the blue laser light source 45, and a semiconductor light emitting element LD2 having a central wavelength of 446 nm is provided as a light emission source of the blue laser light source 47. In addition, each of the semiconductor light emitting elements LD1 and LD2 is individually controlled by a light source control section 49, and the light amount ratio between the light emitted from the blue laser light source 45 and the light emitted from the blue laser light source 47 is individually changeable.

The semiconductor light emitting elements LD1 and LD2 may use an InGaN-based laser diode of a broad area type, and also may use an InGaNAs-based laser diode or a GaNAs-based laser diode. In addition, as the above-described light source, a light emitting member such as a light emitting diode may be used.

In the blue laser lights emitted from the blue laser light sources 45 and 47, each of the emission wavelengths is measured in advance, and the emission wavelength is stored in a storage section 75 connected to the light source control section 49.

The blue laser lights emitted from the light sources 45 and 47 are respectively input to optical fibers 55A and 55B by a condensing lens (not shown), and are propagated to the connector 25A via a combiner 51 as a multiplexer and a coupler 53 as a demultiplexer. In addition, the invention is not limited thereto, but has a configuration in which the laser lights emitted from the light sources 45 and 47 are directly supplied to the connector 25A without using the combiner 51 and the coupler 53.

The blue laser light obtained by multiplexing two blue laser lights having a central wavelength of 445 nm is propagated to the connector 25A, and is propagated to the endoscope front end portion 35 of the endoscope 11 by the optical fibers 55A and 55B. Then, the blue laser light excites a fluorescent substance 57, which is a wavelength converting member disposed in the light emitting ends of the optical fibers 55A and 55B of the endoscope front end portion 35, so as to emit light therefrom. Further, a part of the blue laser light directly passes through the fluorescent substance 57.

The fluorescent substance 57 includes plural types of fluorescent substances (for example, a YAG-based fluorescent substance or a fluorescent substance such as BAM ($BaMgAl_{10}O_{17}$)) which absorbs a part of the blue laser light and is excited to emit light as green to yellow. Accordingly, the blue laser light is changed to white (color similar to white) illumination light by mixing green to yellow excitation light as the excitation light with the blue laser light not absorbed and transmitted by the fluorescent substance 57. Like the example of the configuration, when the semiconductor light emitting elements LD1 and LD2 are used as an excitation light source, it is possible to obtain a white light having a high emission efficiency and a high intensity. Also, it is possible to easily control the intensity of the white light, and to minimally suppress variation in the color temperature and chromaticity of the white light.

The fluorescent substance 57 may prevent an occurrence of flickering when performing a video display or overlapping of noise as a barrier in the imaging operation due to a speckle generated by coherence of laser light. In addition, in the fluorescent substance 57, in consideration of differences in the refractive index between the fluorescent material forming the fluorescent substance and a fixing/solidifying resin as a filling agent, it is desirable that the particles of the filling agents and the fluorescent material are formed of a material having large scattering and small absorption with respect to the infrared light. Accordingly, it is possible to improve the scattering effect without reducing the light intensity with respect to the light of red or infrared region, and to reduce the optical loss.

The optical fibers 55A and 55B are multi-mode fibers. As an example, a thin fiber cable may be used which has a core diameter of 105 μm, a cladding diameter of 125 μm, and a diameter of 00.3 to 0.5 mm including a protection layer as an outer surface.

Figure 3:
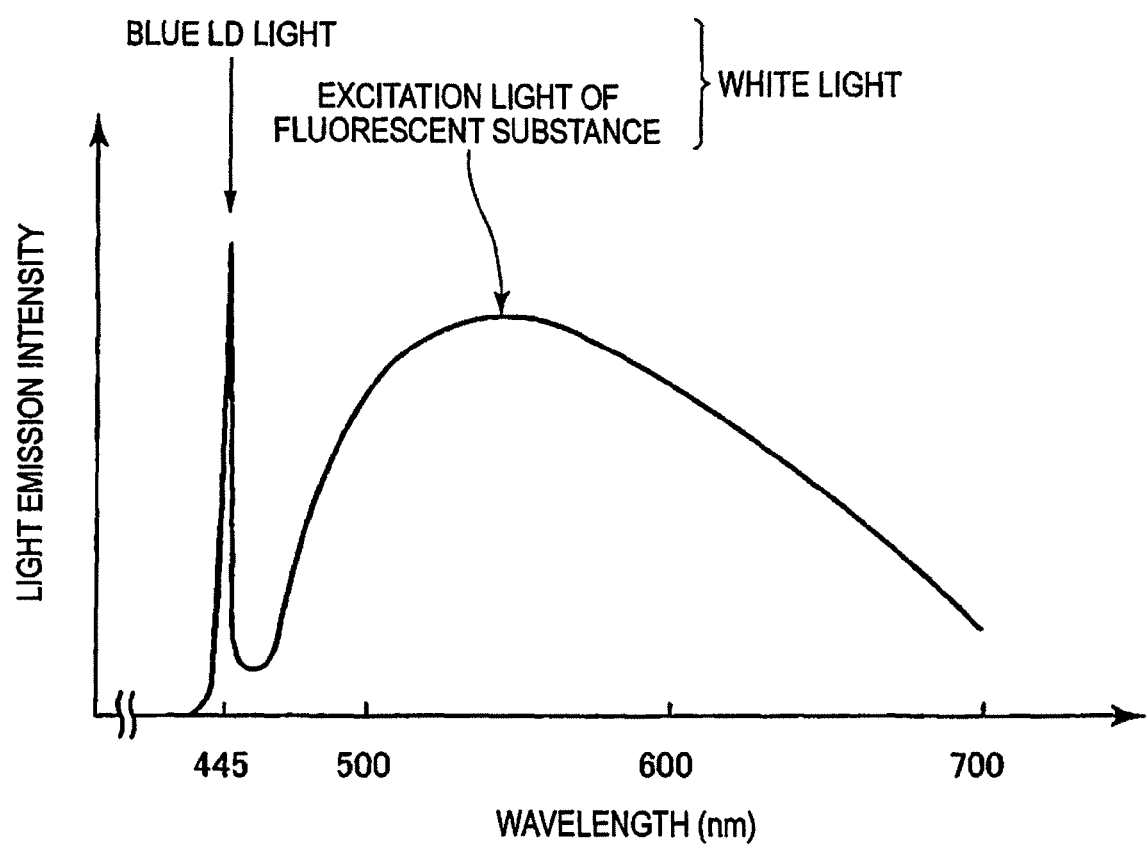
FIG. 3 is a graph showing a light emission spectrum of a blue laser light generated from a blue laser light source and a light emission spectrum in which the wavelength of the blue laser light is converted by a fluorescent substance.

FIG. 3 is a graph showing a light emission spectrum of a blue laser light generated from a blue laser light source and a light emission spectrum in which the wavelength of the blue laser light is converted by a fluorescent substance. The blue laser light is depicted by the bright line having a central wavelength of 445 nm, and the excitation light emitted from the fluorescent substance 57 by the blue laser light has a spectral intensity distribution in which the light emission intensity substantially increases in the bandwidth of the wavelength of 450 nm to 700 nm. The above-described white light is formed by the profile of the excitation light and the blue laser light.

Accordingly, the white light mentioned in the specification precisely includes not only all the wavelength components of visible light, but also for example, R, G, B, and the like of light of a specific wavelength. For example, light including a wavelength component from green to red or the light including the wavelength component from blue to green is in a broad sense included in the white light.

In the endoscope apparatus 100, the emission intensity of the profile shown in FIG. 3 is controlled to be increased and decreased by the light source control section 49, thereby generating illumination light having arbitrary luminance balance.

Here, the profile shown in FIG. 3 will be described in more detail with reference to FIGS. 4 and 5.

Figure 4:
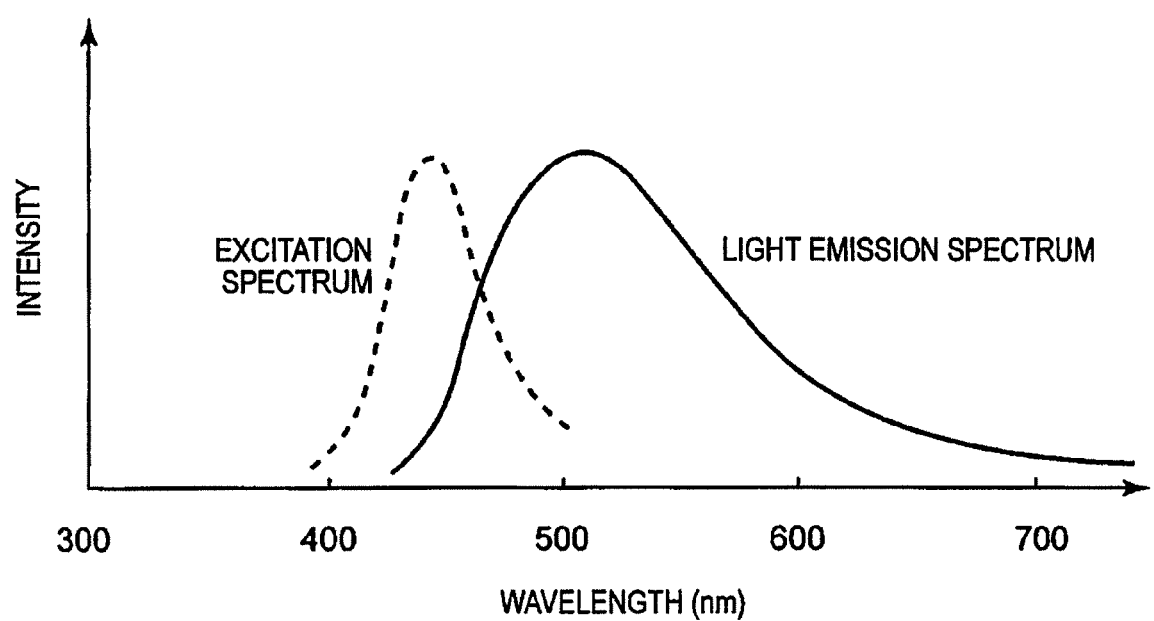
FIG. 4 is a graph showing an example of an excitation spectrum and an emission spectrum of a fluorescent substance.
Figure 5:
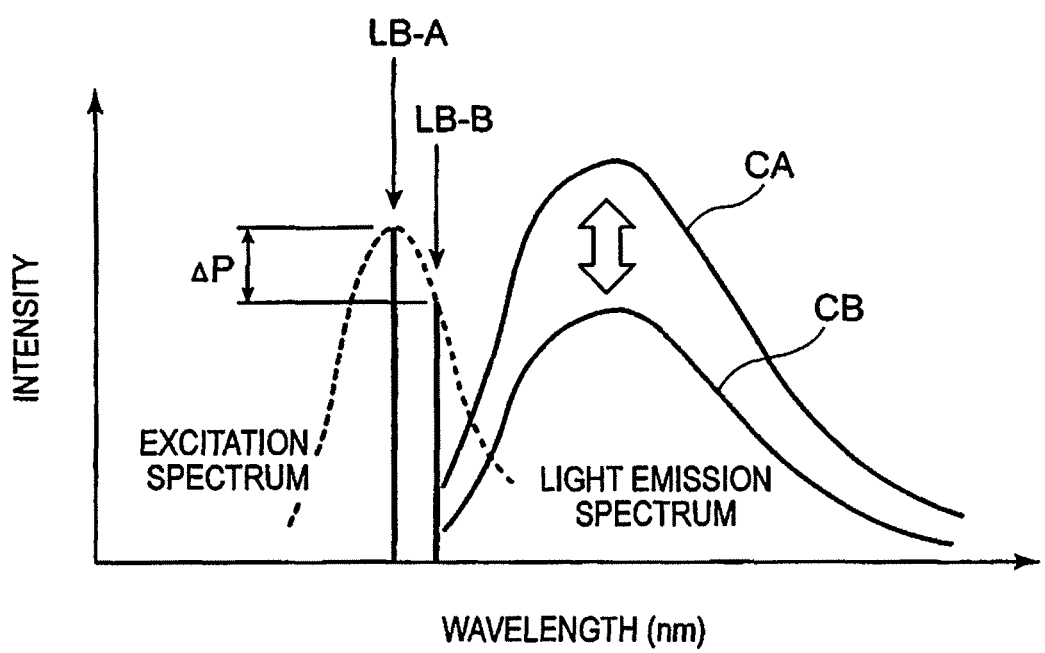
FIG. 5 is an explanatory diagram showing that the light emission intensity of a fluorescent substance is changed in accordance with the magnitude of absorbed energy.

FIG. 4 is a graph showing an example of an excitation spectrum and a light emission spectrum of a fluorescent substance. In the fluorescent substance of this case, the excitation spectrum indicated by the dotted line is allowed to absorb the light in the bandwidth of the wavelength of about 420 to 470 nm, and particularly to absorb the light of the wavelength of about 445 nm with high efficiency. The fluorescent substance 57 is excited by the absorbed excitation light, and emits fluorescence of the spectrum depicted by the light emission spectrum indicated by the solid line.

The light emission intensity of the fluorescent substance 57 is changed in accordance with the magnitude of the absorbed energy. For example, as shown in FIG. 5, if it is assumed that the light emission wavelength of the blue laser light source is deviated, in the laser beam LB-A of the stipulated wavelength of 445 nm, highly efficient absorption occurs at a wavelength at which the excitation spectrum substantially reaches the peak. However, in the laser beam of LB-B, since the light emission wavelength is deviated, the intensity of the excitation spectrum is decreased by ΔP. Then, in the laser beam LB-B, the light intensity is the same as that of the laser beam LB-A, and the light emission spectrum of the fluorescent substance is decreased from CA to CB, which causes a relative difference in the light emission intensity of the fluorescent substance.

Then, in the white light formed by the light emission of the fluorescent substance and the blue laser light, the tone of the white light is changed due to a variation in the intensity balance of the light emission (a variation in accordance with the wavelength) of the fluorescent substance and the blue laser light (uniform intensity). That is, in the case where the light emission wavelength is deviated as in the laser beam LB-B, the light emission intensity of the fluorescent substance is decreased, and the intensity ratio of the blue laser light is relatively increased, which makes the bluish-white light.

Likewise, in order to make the tone of the illumination light uniform, it is necessary to make the wavelength of the laser light source uniform with high precision. For this reason, in the endoscope apparatus with such a configuration, a plurality of laser light sources is used, and the respective laser lights are multiplexed, thereby reducing the influence caused by individual differences of the wavelengths of the emission lights included in the laser light sources. By multiplexing the laser lights output from the plurality of laser light sources, it is possible to set the central wavelength of the multiplexed laser light to the average wavelength of the respective laser light sources, that is, the wavelength substantially equal to the stipulated wavelength (445 nm)

Returning to FIG. 1, the description thereof is continued. As described above, the white illumination light formed by the excitation light emitted from the fluorescent substance 57 and the blue laser light is emitted from the front end portion 35 of the endoscope 11 to the observation area of the test object. Then, the image of the observation area illuminated by the illumination light is formed on the light receiving surface of the imaging element 21 by the use of the object lens unit 39.

The image signal of the captured image output from the imaging element 21 after the imaging operation thereof is transmitted to an A/D converter 65 via a scope cable 63 and is converted into a digital signal. Then, the digital signal is input to an image processing section 67 of the processor 43 via the connector 25B. The image processing section 67 converts the input digital image signal into image data. The converted image data is appropriately subjected to an image process by the image processing section 67, and is output to a desired output image information control section 73.

The output image information input to the control section 73 is displayed as an endoscope observation image in the display unit 15, and is stored in the storage section 75 including a memory or a storage device, if necessary.

Next, the multiplexing operation of the laser lights emitted from two blue laser light sources 45 and 47 having slightly different light emission wavelengths will be described.

FIGS. 6A to 6D show a spectrum of a synthetic laser light obtained by multiplexing two laser lights having different light emission wavelengths and light emission intensities.

Figure 6A:
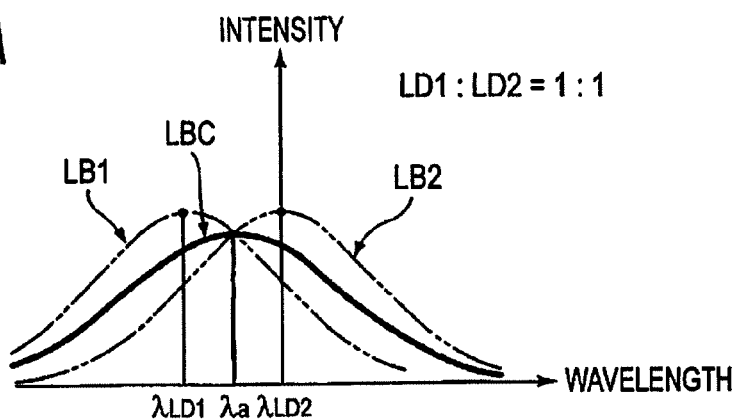
FIGS. 6A to 6D are graphs showing spectrums of synthetic laser lights formed by multiplexing two laser lights having different light emission wavelengths and light emission intensities in accordance with predetermined light amount ratios.

As shown in FIG. 6A, the synthetic laser light LBC of the spectrum depicted by the solid line may be obtained by multiplexing the blue laser light LB1 having the central light emission wavelength $\lambda_{LD2}$ emitted from one blue laser light source 47 depicted by the one-dotted dashed line and the blue laser light LB2 having the central light emission wavelength $\lambda_{LD1}$ emitted from the other blue laser light source 45 depicted by the two-dotted dashed line and having the central wavelength shorter than that of the blue laser light LB1. In addition, each of the light emission wavelengths $\lambda_{LD1}$ and $\lambda_{LD2}$ of two blue laser lights LB1 and LB2 emitted from the blue laser light sources 45 and 47 is a uniform wavelength. In addition, in FIGS. 6A to 6D, for easy comparison with the light emission wavelengths of the blue laser lights LB1 and LB2, the scale of the light emission intensity of the synthetic laser light LBC is depicted to be ½.

FIG. 6A shows the spectrum of the synthetic laser light LBC when the blue laser lights LB1 and LB2 having the same light amount ratio (LD1:LD2=1:1) are emitted from the blue laser light sources 45 and 47. At this time, the central wavelength $\lambda a$ of the synthetic laser light LBC is a middle value between the central wavelengths $\lambda_{LD1}$ and $\lambda_{LD2}$ of the blue laser lights LB1 and LB2.

Figure 6B:
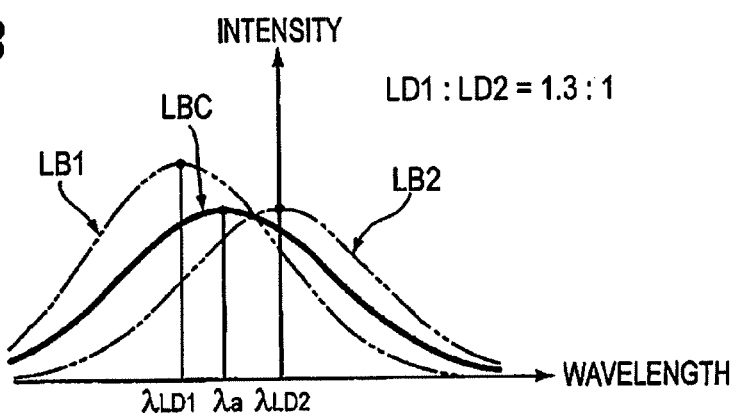

FIG. 6B shows the spectrum in the case where the lights are respectively emitted from the blue laser light sources 45 and 47 so as to have a different light amount ratio therebetween, and the light amount ratio is set to LD1:LD2=1.3:1. At this time, the central wavelength $\lambda b$ of the synthetic laser light LBC is shifted to the central wavelength $\lambda_{LD1}$ of the blue laser light LB1 having strong intensity from the middle value between the central wavelengths $\lambda_{LD1}$ and $\lambda_{LD2}$ of the blue laser lights LB1 and LB2.

Figure 6C:
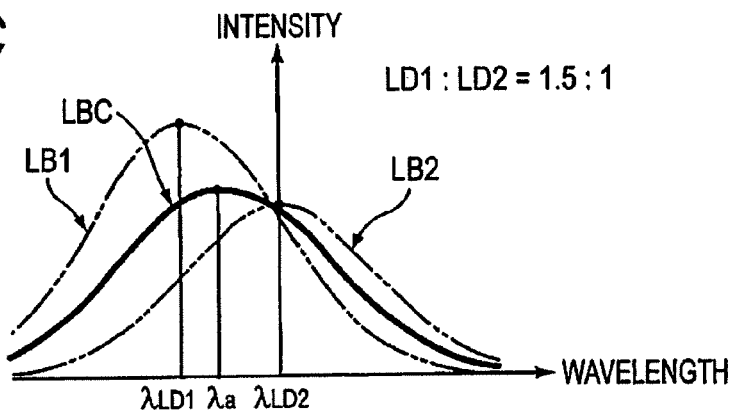
Figure 6D:
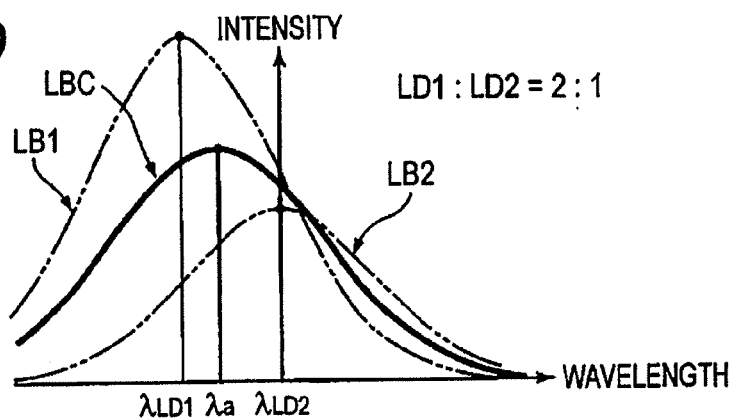

Also, FIG. 6C shows the spectrum in the case where the lights are respectively emitted from the blue laser light sources 45 and 47 so as to have a light amount ratio of LD1:LD2=1.5:1. FIG. 6D shows the spectrum in the case where the lights are respectively emitted from the blue laser light sources 45 and 47 so as to have a light amount ratio of LD1:LD2=2.0:1. Here, the central wavelengths of the synthetic laser lights LBC are $\lambda c$ and $\lambda d$, and are further shifted to the central wavelength $\lambda_{LD1}$ of the blue laser light LB1.

Figure 7:
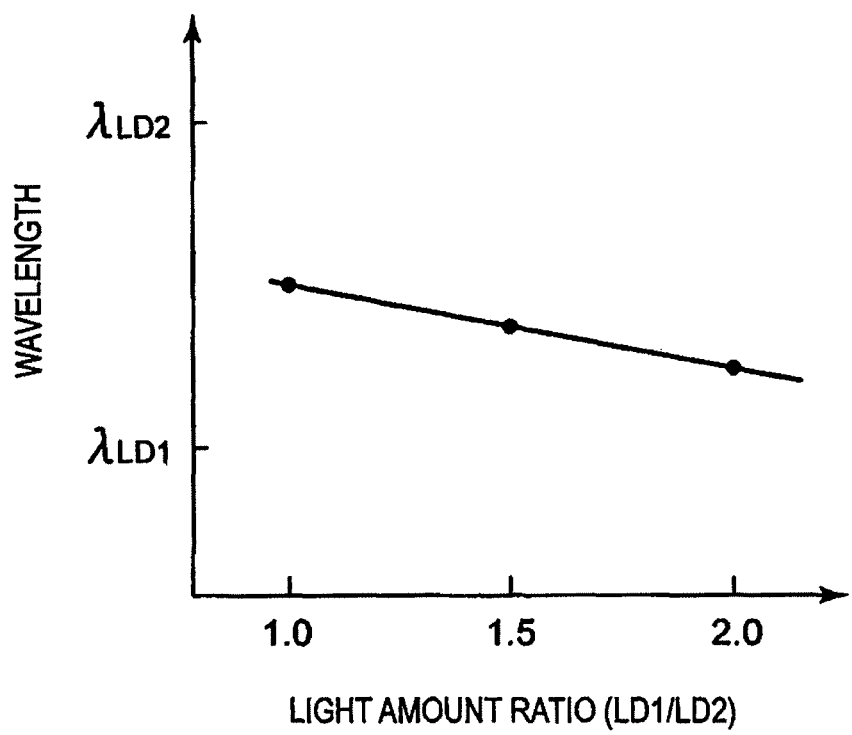
FIG. 7 is a graph showing a relationship between the light amount ratio and the central wavelength of synthetic laser light when light emission wavelengths of two laser lights having different wavelengths are set to be uniform.

FIG. 7 is a graph showing a relationship between the light amount ratio of the blue laser lights LB1 and LB2 having the central wavelengths $\lambda_{LD1}$ and $\lambda_{LD2}$ emitted from the blue laser light sources 45 and 47 and the central wavelength of the synthetic laser light LBC. When light emission wavelengths $\lambda_{LD1}$ and $\lambda_{LD2}$ of the blue laser light sources 45 and 47 are respectively set to be uniform, the central wavelength of the synthetic laser light LDC is shifted to the wavelength in which the intensity is increased. In other words, when the light amount ratio of the respective blue laser lights is controlled, it is possible to set the central wavelength of the synthetic laser light to an arbitrary wavelength between the light emission wavelengths of the respective blue laser lights.

Figure 8:
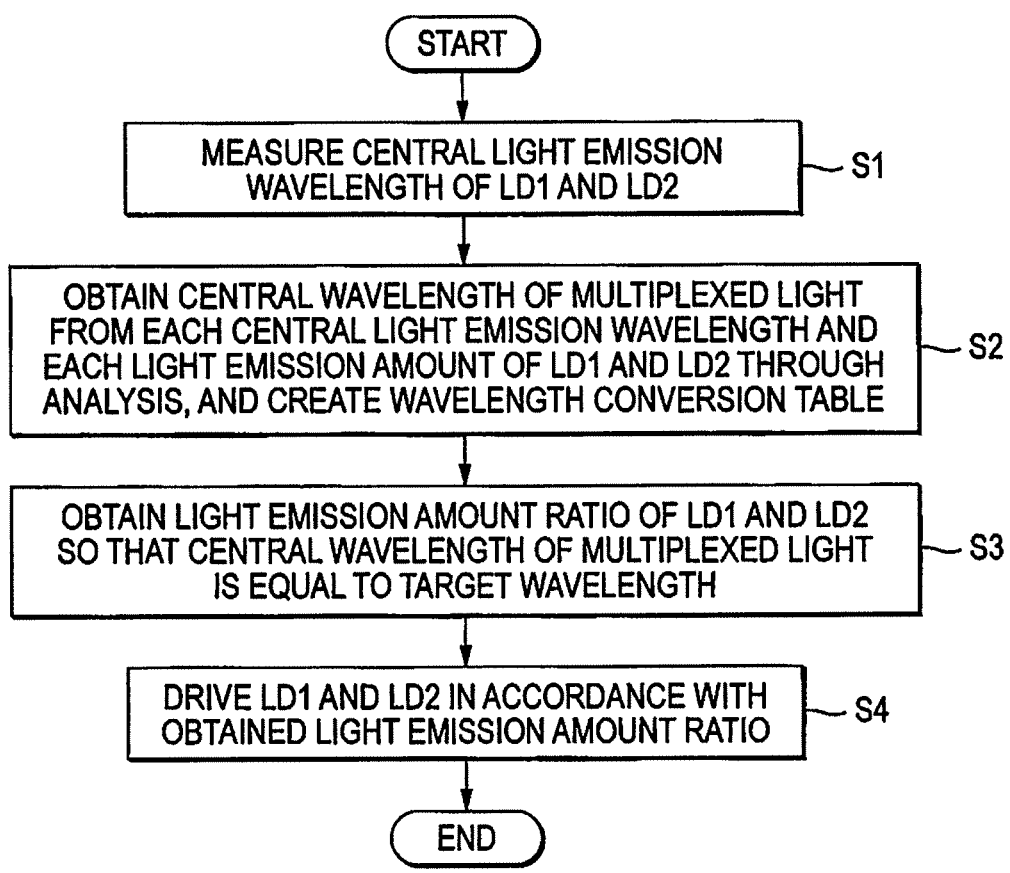
FIG. 8 is a flowchart showing a procedure of obtaining synthetic laser light having a desired wavelength by multiplexing two laser lights having different light emission intensities.

Next, a driving procedure of the blue laser light sources 45 and 47 (LD1 and LD2) for adjusting the wavelength of the synthetic laser light to be a desired wavelength in the endoscope apparatus 100 will be described in detail with reference to the flowchart of FIG. 8.

First, the central wavelengths $\lambda_{LD1}$ and $\lambda_{LD2}$ emitted from two semiconductor light emitting elements LD1 and LD2 are respectively measured by a wavelength measurement device (Step S1). Then, the central wavelength of the synthetic laser light when changing the light emission amount of each of the LD1 and LD2 is obtained through analysis from the measured central wavelengths, a wavelength conversion table showing a relationship between the light amount ratio of the LD1 and LD2 and the wavelength of the synthetic laser light is created, and then the wavelength conversion table is stored in the storage section 75 shown in FIG. 1 (Step S2). It is desirable that the operations in Steps S1 and S2 are performed during the manufacturing process of the endoscope apparatus 100, that is, the time until the shipment of the product.

Then, when a switch 79 (refer to FIG. 1) disposed in the operation unit 23 is operated during the usage of the endoscope apparatus 100, this operation is considered as a calibration start point. Accordingly, the light source control section 49 obtains the light amount ratio of the laser lights to be emitted from the light sources LD1 and LD2 so that the central wavelength of the synthetic laser light is equal to the target wavelength by referring to the wavelength conversion table registered in the storage section 75 (Step S3), and drives the light sources LD1 and LD2 in accordance with the light amount ratio (Step S4). Accordingly, the central wavelength of the synthetic laser light is controlled to be equal to the arbitrary wavelength as the target. The target wavelength is basically set as an original value in the endoscope apparatus 100. However, for example, the target wavelength may be set in accordance with the type of the endoscope 11 connected to the control device 13 shown in FIG. 1, or may be set to an arbitrary value which is input from the outside.

Incidentally, the semiconductor light emitting elements LD1 and LD2 used as the light emission sources of the blue laser light sources 45 and 47 are divided into groups in accordance with the light emission wavelength through a product inspection step in the manufacturing process. For example, there are divided groups such that one standard group equal to or more than 444 nm and less than 446 nm includes the central wavelength of 445 nm, and the other group is not included in the range. Generally, only the semiconductor light emitting elements LD1 and LD2 of the standard group are used while being mounted to the light source device 41, and the semiconductor light emitting elements LD1 and LD2 of the other group (out of the standard group) are not used in this kind of light source device 41. However, according to the endoscope apparatus 100 with such a configuration, even the semiconductor light emitting elements LD1 and LD2 out of the standard group may be actively used as the illumination light source.

That is, in the case where the semiconductor light emitting elements LD1 and LD2 out of the standard group are divided into a first short wavelength group equal to or more than 440 nm and less than 444 nm and a second long wavelength group equal to or more than 446 nm and less than 449 nm, the semiconductor light emitting elements LD1 and LD2 are respectively extracted from the first group and the second group, and are used as the light emission sources of the above-described blue laser light sources 45 and 47.

In other words, a pair of the semiconductor light emitting element LD1 having the central light emission wavelength closer to the short wavelength than the stipulated light emission wavelength and the semiconductor light emitting element LD2 closer to the long wavelength is used, the central wavelength of the synthetic laser light when changing the light emission wavelengths and the light emission amounts thereof is obtained through analysis, and the central wavelength is stored in the wavelength conversion table. Then, as described above, the light source control section 49 controls the light emission intensities of the semiconductor light emitting elements LD1 and LD2 on the basis of the wavelength conversion table so that the central wavelength of the synthetic laser light is equal to a predetermined light emission wavelength. Accordingly, even the semiconductor light emitting elements LD1 and LD2 not considered as the standard products may be used as the light emission sources of the blue laser light sources 45 and 47 which are required to supply illumination lights having stipulated wavelengths with high precision to the endoscope front end portion 35, and the cost of the endoscope apparatus 100 may be reduced.

Even in the light source device 41 for performing white illumination by exciting the fluorescent substance 57 using the blue laser light to emit light therefrom, in the case where the absorption spectrum of the fluorescent substance 57 is formed as a steep profile in the blue wavelength bandwidth, the light emission efficiency of the fluorescent substance 57 is increased or decreased in accordance with a slight variation in the wavelength of the blue laser light sources 45 and 47. As a result, even when the fluorescent substance 57 is illuminated by the same light emission intensity, the light emission amount of the fluorescent substance 57 is decreased, which may cause a bluish-white illumination. However, according to the endoscope apparatus 100 with such a configuration, since the central wavelength of the synthetic laser light may be controlled with high precision to be an arbitrary wavelength as a target, the light emission spectrum illuminates uniform white light, thereby displaying the observation image on the display unit 15 with satisfactory tone at all times.

Figure 9:
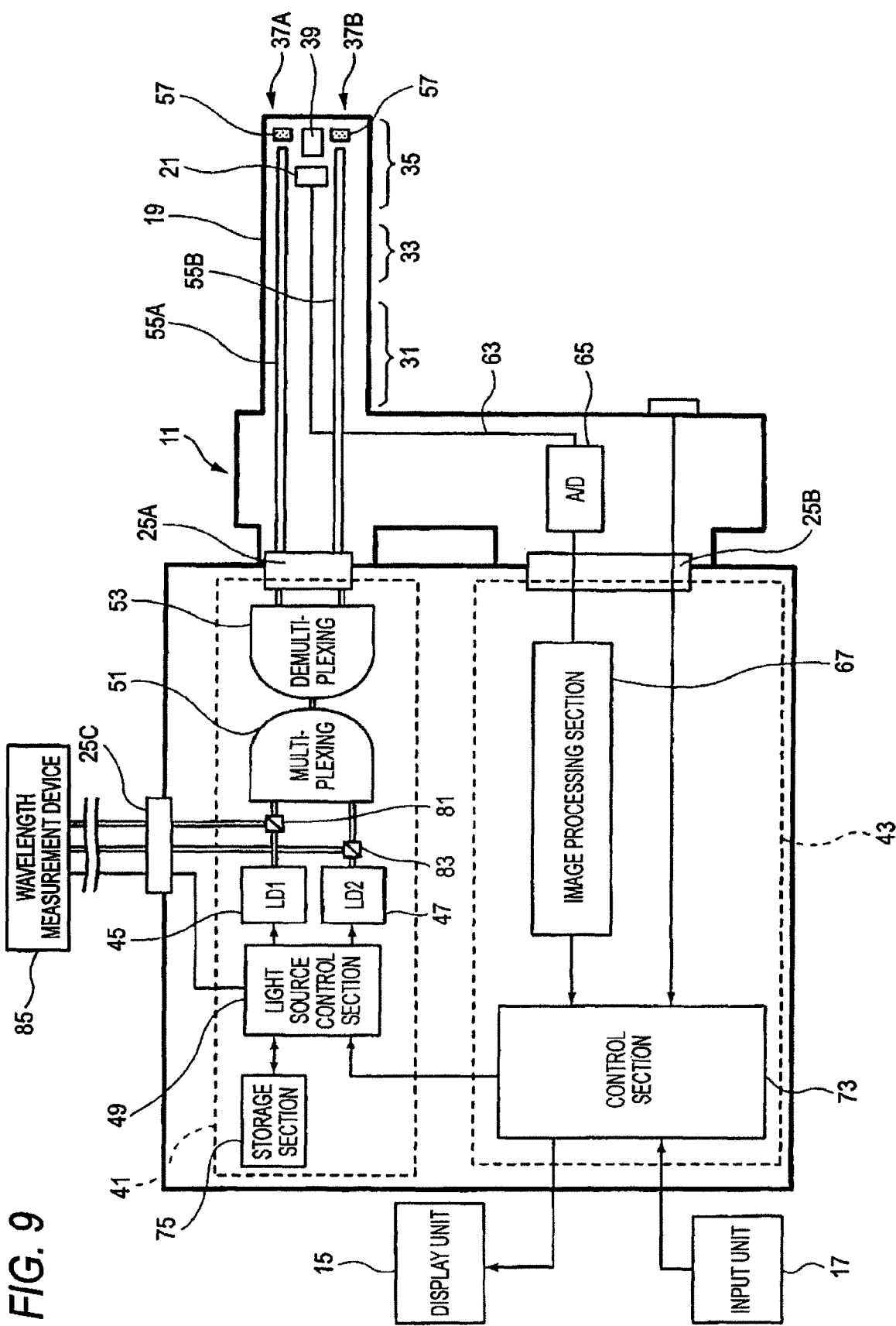
FIG. 9 is a conceptual block diagram of the endoscope apparatus of a modified example 1.

In addition, the light emission wavelengths of the above-described semiconductor light emitting elements LD1 and LD2 may be measured at an appropriate timing, and the information of the storage section 75 may be rewritten. FIG. 9 is a conceptual block diagram of the endoscope apparatus 100 of the modified example 1 in which the information of the storage section 75 may be rewritten. In FIG. 9, since the same reference numerals are given to the same components as those shown in FIG. 1, the description thereof is omitted.

As shown in FIG. 9, in the endoscope apparatus 100 of the modified example 1, reflection means 81 and 83 such as a beam splitter or a galvanic mirror are disposed in the course of the light path connecting the blue laser light sources 45 and 47 to the combiner 51 as the multiplexer. The laser lights emitted from the blue laser light sources 45 and 47 exit from the light path while being reflected by the reflection means 81 and 83, and are output to the connector 25C installed in the control device 13.

Then, the wavelengths of the laser lights of the blue laser light sources 45 and 47 are measured by the wavelength measurement device 85 connected to the connector 25C, and the measurement result is written to the storage section 75 via the light source control section 49. Accordingly, even in the case where there is a variation in the characteristics of the semiconductor light emitting elements LD1 and LD2, or the semiconductor light emitting elements LD1 and LD2 are exchanged with another by maintenance and the like after the shipment of the endoscope apparatus 100, it is possible to supply the illumination light having an accurate stipulated wavelength at all times, and to display an image having a correct color on the display unit 15. In the application field of the endoscope apparatus 100, it is easy to perform a periodic calibration. The writing process to the storage section 75 may be performed in a manufacture factory after transporting the endoscope apparatus 100 to manufacturing factory, or may be performed in the application field.

Figure 10:
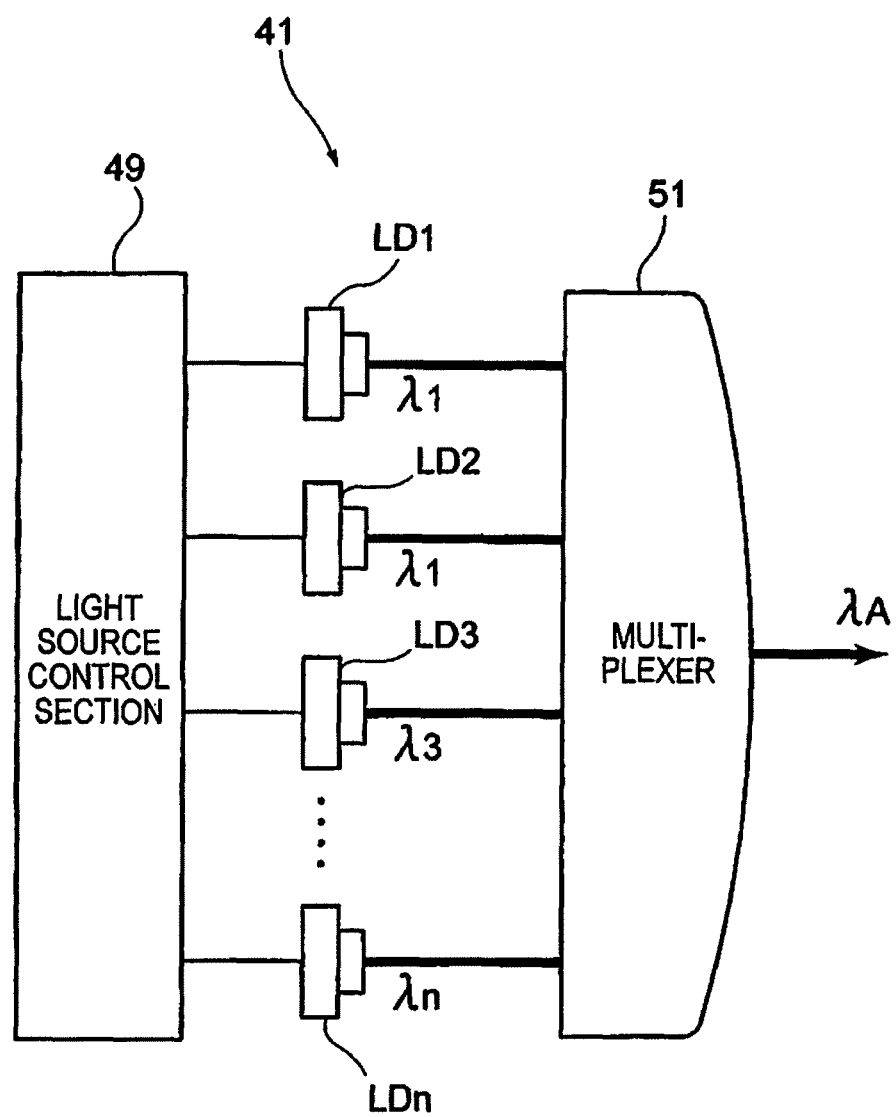
FIG. 10 is a block diagram showing a configuration of a main part of a light source device of a modified example 2.

In addition, the configuration of the endoscope apparatus 100 may be modified into various forms. For example, the number of the semiconductor light emitting elements LD used for the multiplexing operation is not limited to two of the above-described LD1 and LD2, but may be an arbitrary number. FIG. 10 is a block diagram showing a configuration of a main part of the light source device of the modified example 2, where one light source device 41 is provided with n number of light emitting elements LD1, LD2, LD3, . . . , LDn, and the laser lights respectively emitted from the n number of semiconductor light emitting elements LD1, LD2, LD3, . . . , LDn are multiplexed by the combiner 51. When the laser lights emitted from the plurality of semiconductor light emitting elements LD1, LD2, Ld3, . . . , LDn are multiplexed, it is possible to allow the spectral profile of the synthetic laser light to be close to the smoother Gauss distribution profile compared with the case where two semiconductor light emitting elements LD1 and LD2 are used. At this time, it is desirable to use the combination of the light sources having different light emission wavelengths $\lambda_1$ to $\lambda_n$ so that the adjustment bandwidth of the wavelength of the multiplexed light becomes large.

Figure 11:
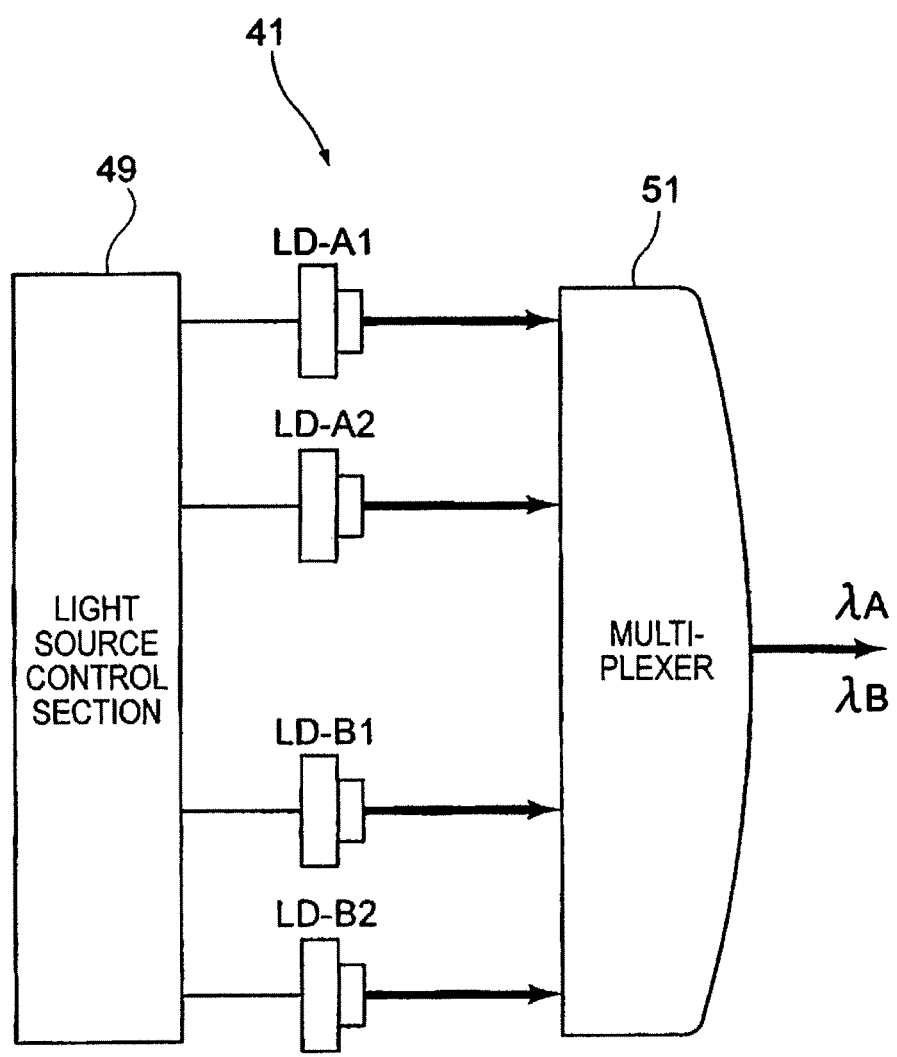
FIG. 11 is a block diagram showing a configuration of a main part of a light source device of a modified example 3.

FIG. 11 is a block diagram showing a configuration of a main part of the light source device of the modified example 3, where the light sources LD used for the multiplexing operation may be the light sources having plural types of wavelength bandwidths. In the modified example 3 shown in FIG. 11, one light source device 41 is provided with the combination of two semiconductor light emitting elements LD-A1 and LD-A2 having a stipulated wavelength of 445 nm and another two semiconductor light emitting elements LD-B1 and LD-B2 having a stipulated wavelength of 405 nm. When the laser lights respectively emitted from these four semiconductor light emitting elements LD-A1, LD-A2, LD-B1, and LD-B2 are multiplexed by the combiner 51, the wavelength $\lambda_A$ averaged around the wavelength of 445 nm and the wavelength $\lambda_B$ averaged around the wavelength of 405 nm are formed.

In this case, when the lights emitted from the plurality of semiconductor light emitting elements stipulated to have the same wavelength are multiplexed, it is possible to absorb differences in the wavelength caused by individual differences of each of the semiconductor light emitting elements, and to arrange the wavelengths of the illumination lights. For example, the standard light emission wavelengths of the semiconductor light emitting elements LD-A1 and LD-A2 are 445 nm, but in actual application, the semiconductor light emitting elements have individual differences due to differences in manufacturing. For this reason, the semiconductor light emitting elements may emit lights having wavelengths deviating from 445 nm by, for example, ±5 nm. Accordingly, as shown in FIG. 11, the lights of the plurality of semiconductor light emitting elements LD-A1 and LD-A2 are multiplexed and used, and in the same way, the lights of the plurality of semiconductor light emitting elements LD-B1 and LD-B2 are multiplexed and used, thereby averaging differences in the wavelength of the semiconductor light emitting element. As a result, the wavelengths of the multiplexed lights are 445 nm and 405 nm, and differences in the light emission wavelength and the like caused by individual differences may be reduced compared with the case where one laser light source is used.

Likewise, the present invention is not limited to the above-described embodiment, but corrections and applications thereof may be made by the person skilled in the art on the basis of the description of the specification and the known technology, and those are included in the scope required to be protected.

As described above, the present specification discloses the following items.

(1) An endoscope apparatus including: an endoscope which includes an illumination optical system having a fluorescent substance; a light source unit which is connected to the endoscope, includes a plurality of semiconductor light emitting elements having different central light emission wavelengths, and supplies light from the semiconductor light emitting elements to the illumination optical system; a multiplexer means for multiplexing the lights output from the plurality of semiconductor light emitting elements; and a central wavelength converting means for controlling a light emission amount ratio of the plurality of semiconductor light emitting elements and converting the central wavelength of the light multiplexed by the multiplexer means.

According to the endoscope apparatus, it is possible to highly precisely maintain the wavelength of the light emitted from the semiconductor light emitting element to be a stipulated constant value, and to generate light of a stipulated wavelength even in the single semiconductor light emitting element of which the light emission wavelength is not included in the stipulated wavelength range. Accordingly, it is possible to prevent deterioration in the illumination light amount or imaging sensitivity, and to reduce the cost of components of the endoscope apparatus.

(2) The endoscope apparatus according to (1), wherein the central wavelength converting means has a wavelength conversion table in which the central wavelength of the light formed by multiplexing the lights emitted from the plurality of semiconductor light emitting elements is obtained on the basis of information of the light emission amounts and the central light emission wavelengths of the plurality of semiconductor light emitting elements, and the light emission amount ratio of the semiconductor light emitting elements is determined by referring to the wavelength conversion table.

According to the endoscope apparatus, the wavelength conversion table is created, and the light emission amount of each of the semiconductor light emitting elements is controlled on the basis of the wavelength conversion table. Accordingly, it is possible to simply adjust the wavelength of the light emitted from the semiconductor light emitting element at an arbitrary timing.

(3) The endoscope apparatus according to (1), wherein a plurality of the fluorescent substances is disposed at different positions of an endoscope front end portion inserted into a test object, and wherein the endoscope apparatus further includes a demultiplexer means which demultiplexes the multiplexed light and supplies the demultiplexed light to each of the plurality of fluorescent substances.

According to the endoscope apparatus, the plurality of fluorescent substances are disposed at the plurality of positions of the endoscope front end portion, and the light demultiplexed by the demultiplexer means is supplied to each of the fluorescent substances. Accordingly, it is possible to illuminate the test object with uniform illumination light without generating shadows on the test object.

(4) The endoscope apparatus according to (1), further including: an output light extracting means for individually extracting the lights output from the plurality of semiconductor light emitting elements in the course of an optical path; and a wavelength measurement means for measuring the wavelength of each of the lights extracted by the output light extracting means, wherein the central wavelength converting means determines the light emission amount ratio on the basis of the wavelength measurement values of the lights emitted from the plurality of semiconductor light emitting elements.

According to the endoscope apparatus, the wavelength of the light emitted from each of the semiconductor light emitting elements is measured, and the light emission amount ratio is controlled on the basis of the wavelength measurement value. Accordingly, it is possible to more accurately adjust the central wavelength of the multiplexed light. Therefore, even in the case where the semiconductor light emitting element is exchanged with another by maintenance and the like, and the characteristics of the semiconductor light emitting element are changed with time, it is possible to more accurately adjust the central wavelength of the multiplexed light.

(5) An illumination control method of an endoscope apparatus including an endoscope which includes an illumination optical system having a fluorescent substance; and a light source unit which is connected to the endoscope, includes a plurality of semiconductor light emitting elements having different central light emission wavelengths, and supplies light from the semiconductor light emitting elements to the illumination optical system, the illumination control method including at least the steps of: measuring the central light emission wavelength of each of the semiconductor light emitting elements; obtaining a central wavelength of light formed by multiplexing the lights output from the plurality of semiconductor light emitting elements through analysis in accordance with setting values of the central light emission wavelength of each of the semiconductor light emitting elements and a light emission amount of each of the semiconductor light emitting elements, and registering the central wavelength in a wavelength conversion table; determining the light emission amount ratio of the semiconductor light emitting elements so that the central wavelength of the multiplexed light is equal to a target wavelength on the basis of the wavelength conversion table; and driving the semiconductor light emitting elements in accordance with the determined light emission amount ratio.

According to the illumination control method of the endoscope apparatus, it is possible to highly precisely generate laser light of a stipulated wavelength from not only a semiconductor light emitting element having the light emission wavelength included in the stipulated wavelength range, but also a single semiconductor light emitting element having a light emission wavelength not included in the stipulated wavelength range. Accordingly, it is possible to prevent deterioration in the illumination light amount or imaging sensitivity, and to reduce the cost of components of the endoscope apparatus.

What is claimed is:

1. An endoscope apparatus including: an endoscope that includes an illumination optical system having at least one of a plurality of fluorescent substance; and a light source unit that is connected to the endoscope, includes a plurality of semiconductor light emitting elements having different central light emission wavelengths, and supplies light from the semiconductor light emitting elements to the illumination optical system; the endoscope system comprising:

a multiplexer, unit that multiplexes the lights output from the plurality of semiconductor light emitting elements;

a central wavelength converting unit that controls a light emission amount ratio of the plurality of semiconductor light emitting elements and converts the central wavelength of the light multiplexed by the multiplexer unit;

wherein the central wavelength converting unit includes a wavelength conversion table in which the central wavelength of the light formed by multiplexing the lights emitted from the plurality of semiconductor light emitting elements is obtained on the basis of information of the light emission amounts and the central light emission wavelengths of the plurality of semiconductor light emitting elements, and the light emission amount ratio of the semiconductor light emitting elements is determined by referring to the wavelength conversion table.

2. The endoscope apparatus according to claim 1, further comprising:

a demultiplexer unit that demultiplexer the multiplexed light output from the multiplexer unit;

wherein the plurality of the fluorescent substances is disposed at different positions of an endoscope front end portion to be inserted into a test object, and the demultiplexer unit supplies the demultiplexed light to each of the plurality of fluorescent substances.

3. The endoscope apparatus according to claim 1, further comprising:

an output light extracting unit that individually extracts the lights output from the plurality of semiconductor light emitting elements in a course of an optical path; and a wavelength measurement unit that measures a wavelength of each of the lights extracted by the output light extracting unit, wherein the central wavelength converting unit determines the light emission amount ratio on the basis of the wavelength measurement values of the lights emitted from the plurality of semiconductor light emitting elements.

4. An illumination control method of an endoscope apparatus including an endoscope that includes an illumination optical system having a fluorescent substance; and a light source unit that is connected to the endoscope, includes a plurality of semiconductor light emitting elements having different central light emission wavelengths, and supplies light from the semiconductor light emitting elements to the illumination optical system, the method comprising at least the steps of:

measuring the central light emission wavelength of each of the semiconductor light emitting elements;

obtaining a central wavelength of light formed by multiplexing the lights emitted from the plurality of semiconductor light emitting elements through analysis in accordance with setting values of the central light emission wavelength of each of the semiconductor light emitting elements and a light emission amount of each of the semiconductor light emitting elements, and registering the central wavelength in a wavelength conversion table;

determining a light emission amount ratio of the semiconductor light emitting elements so that the central wavelength of the multiplexed light is equal to a target wavelength on the basis of the wavelength conversion table; and driving the semiconductor light emitting elements in accordance with the determined light emission amount ratio.

* * * * *